United States Patent [19]

Langhals et al.

[11] Patent Number: 5,981,773
[45] Date of Patent: Nov. 9, 1999

[54] PREPARATION OF PERYLENE-3,4-DICARBOXYLIC ANHYDRIDES

[75] Inventors: Heinz Langhals, Ottobrunn; Petra Christa Von Unold, München; Markus Speckbacher, Mettenheim, all of Germany

[73] Assignee: Ciba Specialty Chemicals Corporation, Tarrytown, N.Y.

[21] Appl. No.: 09/007,195

[22] Filed: Jan. 14, 1998

[30] Foreign Application Priority Data

Jan. 14, 1997 [DE] Germany ............... 197 00 990

[51] Int. Cl.$^6$ ................................. C07D 311/78
[52] U.S. Cl. ............................ 549/381; 546/38
[58] Field of Search ............... 546/38; 549/381

[56] References Cited

U.S. PATENT DOCUMENTS 5,650,513  7/1997  Langals et al. ............. 546/38

FOREIGN PATENT DOCUMENTS 486491   11/1929  Germany .
9622331  7/1996   WIPO .

OTHER PUBLICATIONS

Mol. Cryst. Liq. Cryst., 1988, vol. 158B, pp. 337–352.
Bulletin of the Chemical Society of Japan, vol. 52, (6), pp. 1723–1726, (1979).
Chem. Zentrablatt 1929I, S. 2472.
Liebigs Ann./Recueil, 1997, pp. 467–468.
Chem. Abst 103:87614v, (1985).
Chem. Abst. for DE 486491, vol. 24, p. 1870.
Biochem et al, Chemical Abstract vol. 128 No. 49452, "Preparation of 3,4–perylene dicarboxylic", 1997.

*Primary Examiner*—John Kight
*Assistant Examiner*—Raymond Covington
*Attorney, Agent, or Firm*—David R. Crichton

[57] ABSTRACT

A process for forming perylene-3, 4-dicarboxylic anhydrides by reacting a corresponding perylene-3,4:9, 10-tetracarboxylic dianhydride with a sterically hindered amine, as a base, at an elevated temperature.

11 Claims, No Drawings

PREPARATION OF PERYLENE-3,4-DICARBOXYLIC ANHYDRIDES

The present invention relates to an improved process for the preparation of perylene-3,4-dicarboxylic anhydrides of the general formula I

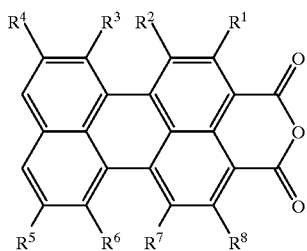

in which $R^1$, $R^2$, $R^3$, $R^4$, $R^5$, $R^6$, $R^7$, $R^8$ are hydrogen, or one radical to eight radicals are a radical selected from the group consisting of an unsubstituted or substituted carbocyclic aromatic radical, an unsubstituted or substituted heterocyclic aromatic radical, halogen, unsubstituted or substituted $C_1$–$C_{18}$alkyl, —$OR^9$, —CN, —$NR^{10}R^{11}$, —$COR^{12}$, —$NR^{13}COR^{12}$, —$NR^9COOR^{12}$, —$NR^9CONR^{10}R^{11}$, —$NHSO_2R^{12}$, —$SO_2R^{12}$, —$SOR^{12}$, —$SO_2OR^{12}$, —$CONR^{10}R^{11}$, —$SO_2NR^{10}R^{11}$, —$N=NR^{14}$, —$OCOR^{12}$ and —$OCONHR^{12}$, where each two adjacent radicals together can form a carbocyclic or heterocyclic ring, where $R^{12}$ is $C_1$–$C_{18}$alkyl, $C_6$–$C_{10}$aryl or benzyl which is unsubstituted or substituted by halogen, $C_1$–$C_4$alkyl or $C_1$–$C_4$alkoxy or is a five- to seven-membered heterocyclic radical, $R^{10}$ and $R^{11}$ independently of one another are hydrogen, $C_1$–$C_{18}$alkyl, $C_3$–$C_{24}$cycloalkyl, $C_6$–$C_{10}$-aryl or 5- to 7-membered heteroaryl, each of which is unsubstituted or substituted by cyano or hydroxyl groups, or in which $R^{10}$ and $R^{11}$ together with at least one of the other radicals $R^1$ to $R^8$ form a 5- or 6-membered carbocyclic or heterocyclic ring, $R^9$ is hydrogen, $C_1$–$C_{18}$alkyl, $C_3$–$C_{24}$cycloalkyl, $C_6$–$C_{10}$aryl or 5- to 7-membered heteroaryl, $R^{13}$ is hydrogen, $C_1$–$C_{18}$alkyl, $C_3$–$C_{24}$cycloalkyl, $C_1$–$C_4$alkylaryl, each of which is unsubstituted or substituted by cyano, hydroxyl or $C_1$–$C_4$alkoxycarbonyl groups, is $C_6$–$C_{10}$aryl which is unsubstituted or substituted by halogen, $C_1$–$C_4$alkyl or $C_1$–$C_4$alkoxy groups, or is a 5- to 7-membered heterocycle, and $R^{14}$ is the radical of a coupling component or $C_6$–$C_{10}$aryl which is unsubstituted or substituted by halogen, $C_1$–$C_4$alkyl or $C_1$–$C_4$alkoxy groups.

Processes for the preparation of perylene-3,4-dicarboxylic anhydrides are known. Thus, for example, in Mol. Cryst. Liqu. Cryst., 158b, (1988), p. 337ff a process is described in which perylene-3,4:9,10-tetracarboxylic bisanhydride is converted into perylene-3,4-dicarboxylic anhydride by gas-phase decarboxylation. However, this procedure is without practical importance because of the low yield (~5%).

Another possible starting material for the preparation of perylene-3,4-dicarboxylic anhydrides is the industrially readily accessible perylene-3,4-dicarboximide. A direct hydrolysis of perylene-3,4-dicarboximides with bases, however, is not possible as the carboximide nitrogen is deprotonated and an imide anion inert to bases such as alkalies is formed.

However, hydrolysis using concentrated sulfuric acid according to the method described in Bull. Chem. Soc. Jpn. 52 (1979) p. 1723ff is possible. Starting from perylene-3,4-dicarboximide, sulfonated perylene-3,4-dicarboxylic anhydride is formed by heating in concentrated sulfuric acid to a temperature of approximately 250° C. The authors have not isolated this intermediate, however, but reacted it further with amines to give perylene-3,4-dicarboximidesulfonic acids substituted on the nitrogen atom and then desulfonated them in order to obtain the corresponding perylene-3,4-dicarboximides substituted on the nitrogen atom. In addition to the involved reaction procedure under drastic conditions (conc. $H_2SO_4$ at 250° C.), the only moderate yields of perylene-3,4-dicarboximides are disadvantageous.

A further process is disclosed in DE-A 4,338,784, according to which N-(2,5-di-tert-butyl-phenyl)perylene-3,4-dicarboximide is prepared in a first step starting from perylene-3,4:9,10-tetracarboxylic bisanhydride. After purification thereof, it is converted into perylene-3,4-dicarboxylic anhydride by treatment with alkali. A disadvantage of this process is that the N-(2,5-di-tert-butylphenyl)perylene-3,4-dicarboximide has to be purified by chromatography.

The partial decarboxylation of perylene-3,4:9,10-tetracarboxylic anhydride with aqueous alkali metal hydroxide to give perylene-3,10-dicarboxylic acid in addition to small amounts of the corresponding 3,9-derivative is known from Chem. Zentralblatt 1929 I, p. 2472.

It was therefore the object of the present invention to make available an improved process for the preparation of perylene-3,4-dicarboxylic anhydrides, which does not have the abovementioned disadvantages. In particular, starting from perylene-3,4:9,10-tetracarboxylic anhydride or its ring-substituted derivatives, the aim was to make accessible perylene-3,4-dicarboxylic anhydride or its ring-substituted derivatives in one reaction step.

Accordingly, the process according to the invention for the preparation of perylene-3,4-dicarboxylic anhydrides of the formula I

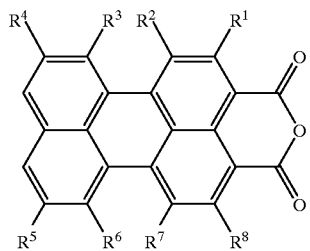

in which $R^1$, $R^2$, $R^3$, $R^4$, $R^5$, $R^6$, $R^7$, $R^8$ are hydrogen, or one radical to eight radicals are a radical selected from the group consisting of an unsubstituted or substituted carbocyclic aromatic radical, an unsubstituted or substituted heterocyclic aromatic radical, halogen, unsubstituted or substituted $C_1$–$C_{18}$alkyl, —$OR^9$, —CN, —$NR^{10}R^{11}$, —$COR^{12}$, —$NR^{13}COR^{12}$, —$NR^9COOR^{12}$, —$NR^9CONR^{10}R^{11}$, —$NHSO_2R^{12}$, —$SO_2R^{12}$, —$SOR^{12}$, —$SO_2OR^{12}$, —$CONR^{10}R^{11}$, —$SO_2NR^{10}R^{11}$, —$N=NR^{14}$, —$OCOR^{12}$ and —$OCONHR^{12}$, where each two adjacent radicals together can form a carbocyclic or heterocyclic ring, where $R^{12}$ is $C_1$–$C_{18}$alkyl, $C_6$–$C_{10}$aryl or benzyl which is unsubstituted or substituted by halogen, $C_1$–$C_4$alkyl or $C_1$–$C_4$alkoxy or is a five- to seven-membered heterocyclic radical, $R^{10}$ and $R^{11}$ independently of one another are hydrogen, $C_1$–$C_{18}$alkyl, $C_3$–$C_{24}$cycloalkyl, $C_6$–$C_{10}$-aryl or 5- to 7-membered heteroaryl, each of which is unsubstituted or substituted by cyano or hydroxyl groups, or in which $R^{10}$ and $R^{11}$ together with at least one of the other radicals $R^1$ to $R^8$ form a 5- or 6-membered carbocyclic or heterocyclic ring, $R^9$ is hydrogen, $C_1$–$C_{18}$alkyl, $C_3$–$C_{24}$cycloalkyl, $C_6$–$C_{10}$aryl or 5- to 7-membered heteroaryl, $R^{13}$ is hydrogen, $C_1$–$C_{18}$alkyl, $C_3$–$C_{24}$cycloalkyl, $C_1$–$C_4$alkylaryl, each of which is unsubstituted or substituted by cyano, hydroxyl or $C_1$–$C_4$alkoxycarbonyl groups, is $C_6$–$C_{10}$aryl which is unsubstituted or substituted by halogen, $C_1$–$C_4$alkyl or $C_1$–$C_4$alkoxy groups, or is a 5- to 7-membered heterocycle, and $R^{14}$ is the radical of a coupling component or $C_6$–$C_{10}$aryl which is unsubstituted or substituted by halogen, $C_1$–$C_4$alkyl or $C_1$–$C_4$alkoxy groups, has been found, which comprises reacting perylene-3,4:9,10-tetracarboxylic anhydride of the formula II

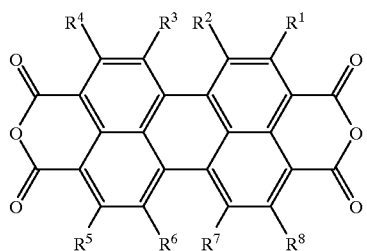

in which $R^1$ to $R^8$ are as defined above, with a sterically hindered amine as a base at elevated temperature.

A selected unsubstituted or substituted carbocyclic aromatic radical can be preferably mono- to tetracyclic, particularly preferably mono- and bicyclic, radicals having five to seven carbon atoms per ring such as phenyl, biphenyl and naphthyl.

A selected unsubstituted or substituted heterocyclic aromatic radical can be preferably a mono- to tricyclic radical having preferably five to seven ring atoms. This radical can consist only of at least one heterocyclic ring or the heterocyclic ring(s) can contain at least one fused benzene ring. Examples which may be mentioned are pyridyl, pyrimidyl, pyrazinyl, triazinyl, furanyl, pyrrolyl, thiophenyl, quinolyl, isoquinolyl, coumarinyl, benzofuranyl, benzimidazolyl, benzoxazolyl, dibenzofuranyl, benzothiophenyl, dibenzothiophenyl, indolyl, carbazolyl, pyrazolyl, imidazolyl, oxazolyl, isoxazolyl, thiazolyl, indazolyl, benzothiazolyl, pyridazinyl, cinnolyl, quinazolyl, quinoxalyl, phthalazinyl, phthalazinedionyl, phthalimidyl, chromonyl, naphtholactamyl, benzopyridonyl, ortho-sulfobenzimidyl, maleimidyl, naphthyridinyl, benzimidazolonyl, benzoxazolonyl, benzothiazolonyl, benzothiazolinyl, quinazolonyl, pyrimidyl, quinoxalonyl, phthalazonyl, dioxapyrinidinyl, pyridonyl, isoquinolonyl, isothiazolyl, benzisoxazolyl, benzisothiazolyl, indazolonyl, acridinyl, acridonyl, quinazolinedionyl, benzoxazinedionyl, benzoxazinonyl and phthalimidyl.

In a preferred embodiment, the carbocyclic and/or heterocyclic aromatic radicals are mono- or polysubstituted by customary substituents, particularly preferably by non-water solubilizing substituents. Examples which may be mentioned are:

halogen such as fluorine, chlorine, bromine and iodine, preferably chlorine;

the cyano group —CN;

unsubstituted or substituted $C_1$–$C_{18}$alkyl such as methyl, ethyl, n-propyl, isopropyl, n-butyl, i-butyl, sec-butyl, tert-butyl, tert-amyl, n-hexyl, 1,1,3,3-tetramethylbutyl, n-heptyl, n-octyl, n-nonyl, n-decyl, n-undecyl, n-dodecyl, n-octadecyl, 3-pentyl, 4-heptyl, 5-nonyl, 6-undecyl, 7-tridecyl, 3-hexyl, 3-heptyl, 3-nonyl, 3-undecyl, preferably $C_1$–$C_{12}$alkyl such as methyl, ethyl, n-propyl, isopropyl, n-butyl, sec-butyl, tert-butyl, tert-amyl, n-hexyl, n-heptyl, n-octyl, n-nonyl, n-decyl, n-undecyl, n-dodecyl, 3-pentyl, 4-heptyl, 5-nonyl, 6-undecyl, 7-tridecyl, 3-hexyl, 3-heptyl, 3-nonyl, 3-undecyl, particularly preferably $C_1$–$C_8$-alkyl such as methyl, ethyl, n-propyl, isopropyl, n-butyl, i-butyl, sec-butyl, tert-butyl, tert-amyl, n-hexyl, 1,1,3,3-tetramethylbutyl, n-heptyl, n-octyl, 3-pentyl, 4-heptyl, 3-hexyl, 3-heptyl, very particularly preferably $C_1$–$C_4$alkyl such as methyl, ethyl, n-propyl, isopropyl, n-butyl, i-butyl, sec-butyl, tert-butyl;

where the alkyl groups mentioned can be substituted by the following groups, which as a rule do not increase the hydrophilicity, such as fluorine, cyano, —OCOR$^{12}$, —OR$^{10}$, —OCOOR$^{12}$, —CON(R$^{10}$)(R$^{11}$) or —OCONHR$^{12}$, in which $R^{12}$ is $C_1$–$C_{18}$alkyl such as methyl, ethyl, n-propyl, isopropyl, n-butyl, i-butyl, sec-butyl, tert-amyl, n-hexyl, 1,1,3,3-tetramethylbutyl, n-heptyl, n-octyl, n-nonyl, n-decyl, n-undecyl, n-dodecyl, n-octadecyl, 3-pentyl, 4-heptyl, 5-nonyl, 6-undecyl, 7-tridecyl, 3-hexyl, 3-heptyl, 3-nonyl, 3-undecyl, preferably $C_1$–$C_{12}$alkyl such as methyl, ethyl, n-propyl, isopropyl, n-butyl, sec-butyl, tert-butyl, tert-amyl, n-hexyl, n-heptyl, n-octyl, n-nonyl, n-decyl, n-undecyl, n-dodecyl, 3-pentyl, 4-heptyl, 5-nonyl, 6-undecyl, 7-tridecyl, 3-hexyl, 3-heptyl, 3-nonyl, 3-undecyl, $C_6$–$C_{10}$aryl such as phenyl, 2,5-di-tert-butylphenyl and naphthyl, preferably phenyl, naphthyl or benzyl which is unsubstituted or substituted by halogen such as chlorine and fluorine, preferably fluorine, $C_1$–$C_4$alkyl or —O—$C_1$–$C_4$alkyl, or a five- to seven-membered heterocyclic radical such as pyridyl, pyrimidyl, pyrazinyl, triazinyl, furanyl, pyrrolyl, thiophenyl, quinolyl, isoquinolyl, coumarinyl, and $R^{10}$ and $R^{11}$ are hydrogen, $C_1$–$C_{18}$alkyl which is unsubstituted or substituted by the cyano or hydroxyl group, as already mentioned above, preferably $C_1$–$C_{12}$alkyl, particularly preferably $C_1$–$C_8$alkyl, very particularly preferably $C_1$–$C_4$alkyl as already mentioned further above, $C_3$–$C_{24}$cycloalkyl, preferably $C_5$-, $C_6$-, $C_{12}$-, $C_{15}$-, $C_{16}$-, $C_{20}$- and $C_{24}$cycloalkyl, aryl or heteroaryl, preferably derived from the abovementioned carboxylic and heterocyclic aromatic radicals, in particular phenyl which is unsubstituted or substituted by halogen, $C_1$–$C_4$alkyl or $C_1$–$C_4$alkoxy, or in which $R^{10}$ and $R^{11}$ together with at least one of the other radicals $R^1$ to $R^8$ form a 5- to 6-membered ring or alternatively heterocyclic ring, for example a pyridine, pyrrole, furan or pyran ring, preferred radicals —OR$^{10}$ are hydroxyl, —O-methyl, —O-ethyl, —O-i-propyl-, —O-i-butyl, —O-phenyl, —O-2,5-di-tert-butylphenyl, preferred radicals —CON(R$^{10}$)(R$^{11}$) are —CONH$_2$, —CONMe$_2$, —CONEt$_2$, —CON(iPr)$_2$, —CON(iBu)$_2$, —CONPh$_2$, —CON(2,5-di-tert-butylphenyl)$_2$.

In a further preferred embodiment, the substituents used on the alkyl groups are mono- or dialkylated amino groups, aryl radicals such as naphthyl or in particular phenyl which is unsubstituted or substituted by halogen, alkyl or —O-alkyl or furthermore heterocyclic aromatic radicals such as 2-thienyl-, 2-benzoxazolyl, 2-benzothiazolyl, 2-benzimidazolyl, 6-benzimidazolonyl, 2-, 3- or 4-pyridinyl, 2-, 4-, or 6-quinolyl or 1-, 3-, 4-, 6- or 8-isoquinolyl radicals.

If the substituents mentioned for their part again contain alkyl, this alkyl can be branched or unbranched and can preferably contain 1 to 18, in particular 1 to 12, especially 1 to 8 and particularly preferably 1 to 4 C atoms. Examples of unsubstituted alkyl groups are methyl, ethyl, n-propyl, isopropyl, n-butyl, sec-butyl, tert-butyl, tert-amyl, n-hexyl, 1,1,3,3-tetramethylbutyl, n-heptyl, n-octyl, n-nonyl, n-decyl, n-undecyl, n-dodecyl, n-octadecyl, 3-pentyl, 4-heptyl, 5-nonyl, 6-undecyl, 7-tridecyl, 3-hexyl, 3-heptyl, 3-nonyl, 3-undecyl, examples of substituted alkyl groups are hydroxymethyl, 2-hydroxyethyl, trifluoromethyl, trifluoroethyl, cyanomethyl, methoxycarbonylmethyl, acetoxymethyl or benzyl.

—$OR^9$, where $R^9$ is hydrogen, $C_1$–$C_{18}$alkyl as already defined for $R^{12}$ including the preferred variants mentioned there, $C_3$–$C_{24}$cycloalkyl, particularly preferably $C_5$-, $C_6$-, $C_{12}$-, $C_{15}$-, $C_{16}$-, $C_{20}$- and $C_{24}$cycloalkyl, $C_6$–$C_{10}$aryl such as naphthyl and phenyl, preferably unsubstituted phenyl and phenyl which is substituted by halogen, $C_1$–$C_4$alkyl or $C_1$–$C_4$-alkoxy, or 5- to 7-membered heteroaryl. Examples of preferred radicals for $R^9$ which may be mentioned are: methyl, ethyl, n-propyl, isopropyl, n-butyl, sec-butyl, tert-butyl, tert-amyl, n-hexyl, 1,1,3,3-tetramethylbutyl, n-heptyl, n-octyl, n-nonyl, n-decyl, n-undecyl, n-dodecyl, n-octadecyl, 3-pentyl, 4-heptyl, 5-nonyl, 6-undecyl, 7-tridecyl, 3-hexyl, 3-heptyl, 3-nonyl, 3-undecyl, hydroxymethyl, 2-hydroxyethyl, trifluoromethyl, trifluoroethyl, cyanomethyl, methoxycarbonylmethyl, acetoxymethyl, benzyl, phenyl, o-, m- or p-chlorophenyl, o-, m- or p-methylphenyl, 1- or 2-naphthyl, cyclopentyl, cyclohexyl, cyclododecyl, cyclopentadecyl, cyclohexadecyl, cycloeicosanyl, cyclotetracosanyl, thienyl and pyranylmethyl; preferred radicals —$OR^9$ are hydroxyl, methoxy, —O-ethyl, —O-i-propyl-, —O-i-butyl, —O-phenyl, —O-2,5-di-tert-butylphenyl;

—$NR^{10}R^{11}$, where $R^{10}$ and $R^{11}$ are as already defined above. Examples of preferred radicals which may be mentioned are: amino, methylamino, dimethylamino, ethylamino, diethylamino, isopropylamino, 2-hydroxyethylamino, 2-hydroxypropylamino, N,N-bis(2-hydroxyethyl)amino, cyclopentylamino, cyclohexylamino, cyclododecylamino, cyclopentadecylamino, cyclohexadecylamino, cycloeicosanylamino, cyclotetracosanylamino, phenylamino, N-methylphenylamino, benzylamino, dibenzylamino, piperidyl or morpholyl;

—$COR^{12}$, where $R^{12}$ is defined as indicated further above. Examples of preferred radicals $R^{12}$ which may be mentioned are: methyl, ethyl, n-propyl, isopropyl, n-butyl, sec- butyl, tert-butyl, tert-amyl, n-hexyl, 1,1,3,3-tetramethylbutyl, n-heptyl, n-octyl, n-nonyl, n-decyl, n-undecyl, n-dodecyl, n-octadecyl, 3-pentyl, 4-heptyl, 5-nonyl, 6-undecyl, 7-tridecyl, 3-hexyl, 3-heptyl, 3-nonyl, 3-undecyl, hydroxymethyl, 2-hydroxyethyl, trifluoromethyl, trifluoroethyl, cyanomethyl, methoxycarbonylmethyl, acetoxymethyl, benzyl, phenyl, o-, m- or p-chlorophenyl, o-, m- or p-methylphenyl, 1- or 2-naphthyl, cyclopentyl, cyclohexyl, cyclododecyl, cyclopentadecyl, cyclohexadecyl, cycloeicosanyl, cyclotetracosanyl, thienyl, pyranylmethyl and furfuryl;

—$NR^{13}COR^{12}$, where $R^{12}$ is defined as indicated further above, and $R^{13}$ is hydrogen, $C_1$–$C_{18}$alkyl, $C_3$–$C_{24}$cycloalkyl, $C_1$–$C_4$alkylaryl, each of which is unsubstituted or substituted by cyano, hydroxyl or $C_1$–$C_4$alkoxycarbonyl groups, is $C_6$–$C_{10}$aryl which is unsubstituted or substituted by halogen, $C_1$–$C_4$alkyl or $C_1$–$C_4$alkoxy groups, or is a 5- to 7-membered heterocycle, where the meaning of the individual radicals such as alkyl, alkoxy, aryl etc. corresponds to the definitions of these radicals indicated further above, including the preferred ranges indicated there. Examples of radicals which may be mentioned are: acetylamino, propionylamino, butyrylamino, benzoylamino, p-chlorobenzoylamino, p-methylbenzoylamino, N-methylacetamino, N-methylbenzoylamino, N-succinimido, N-phthalimido or N-(4-amino)phthalimido;

—$NR^9COOR^{12}$, where $R^{12}$ and $R^9$ are defined as already indicated further above. Examples of radicals which may be mentioned are: —$NHCOOCH_3$, —$NHCOOC_2H_5$ and —$NHCOOC_6H_5$;

—$NR^9CONR^{10}R^{11}$, in which $R^{10}$, $R^{11}$ and $R^9$ are defined as already indicated further above. Examples of radicals which may be mentioned are: ureido, N-methylureido, N-phenyl-ureido or N,N'-2',4'-dimethylphenylureido;

—$NHSO_2R^{12}$, where $R^{12}$ is defined as already indicated further above. Examples of radicals which may be mentioned are: methylsulfonylamino, phenylsulfonylamino, p-tolylsulfonylamino or 2-naphthylsulfonylamino;

—$SO_2R^{12}$, where $R^{12}$ is defined as already indicated further above. Examples of radicals which may be mentioned are: methylsulfonyl, ethylsulfonyl, phenylsulfonyl, 2-naphthylsulfonyl;

—$SOR^{12}$, where $R^{12}$ is defined as already indicated further above. An example of a radical which may be mentioned is phenylsulfoxidyl;

—$SO_2OR^{12}$, where $R^{12}$ is defined as already indicated further above. Examples of radicals $R^{12}$ which may be mentioned are: methyl, ethyl, phenyl, o-, m- or p-chlorophenyl, o-, m- or p-methylphenyl, 1- or 2-naphthyl;

—$CONR^{10}R^{11}$, where $R^{10}$ and $R^{11}$ are defined as already indicated further above. Examples of radicals which may be mentioned are: carbamoyl, N-methylcarbamoyl, N-ethylcarbamoyl, N-phenylcarbamoyl, N,N-dimethylcarbamoyl, N-methyl-N-phenyl-carbamoyl, N-1-naphthylcarbamoyl or N-piperidylcarbamoyl;

—$SO_2NR^{10}R^{11}$, where $R^{10}$ and $R^{11}$ are defined as already indicated further above. Examples of radicals which may be mentioned are: sulfamoyl, N-methylsulfamoyl, N-ethylsulfamoyl, N-phenylsulfamoyl, N-methyl-N-phenylsulfamoyl or N-morpholyl-sulfamoyl;

—$N=NR^{14}$, where $R^{14}$ is the radical of a coupling component or a phenyl radical which is unsubstituted or substituted by halogen, alkyl or —O-alkyl, halogen and alkyl being defined as indicated above. Alkyl occurring in the definitions of $R^{14}$ can have one of the numbers of C atoms indicated further above as preferred. Examples of $R^{14}$ which may be mentioned are: the acetoacetarylide, pyrazolyl, pyridonyl, o-, p-hydroxyphenyl, o-hydroxynaphthyl, p-aminophenyl or p-N,N-dimethylaminophenyl radicals.

—$OCOR^{12}$, where $R^{12}$ is defined as already indicated further above. Examples of radicals $R^{12}$ which may be mentioned are: methyl, ethyl, phenyl, o-, m- or p-chlorophenyl;

—$OCONHR^{12}$, where $R^{12}$ is defined as already indicated further above. Examples of radicals $R^{12}$ which may be mentioned are: methyl, ethyl, phenyl, o-, m- or p-chlorophenyl.

The halogen employed can be fluorine, chlorine, bromine or iodine, preferably fluorine or chlorine.

Unsubstituted or substituted $C_1$–$C_{18}$alkyl which can be employed is methyl, ethyl, n-propyl, isopropyl, n-butyl, i-butyl, sec-butyl, tert-butyl, tert-amyl, n-hexyl, 1,1,3,3-tetramethylbutyl, n-heptyl, n-octyl, n-nonyl, n-decyl, n-undecyl, n-dodecyl, n-octadecyl, 3-pentyl, 4-heptyl, 5-nonyl, 6-undecyl, 7-tridecyl, 3-hexyl, 3-heptyl, 3-nonyl, 3-undecyl, preferably $C_1$–$C_{12}$alkyl such as methyl, ethyl, n-propyl, isopropyl, n-butyl, sec-butyl, tert-butyl, tert-amyl, n-hexyl, n-heptyl, n-octyl, n-nonyl, n-decyl, n-undecyl, n-dodecyl, 3-pentyl, 4-heptyl, 5-nonyl, 6-undecyl, 7-tridecyl, 3-hexyl, 3-heptyl, 3-nonyl, 3-undecyl, particularly preferably $C_1$–$C_8$-alkyl such as methyl, ethyl, n-propyl, isopropyl, n-butyl, i-butyl, sec-butyl, tert-butyl, tert-amyl, n-hexyl, 1,1,3,3-tetramethylbutyl, n-heptyl, n-octyl, 3-pentyl, 4-heptyl, 3-hexyl, 3-heptyl, very particularly preferably $C_1$–$C_4$alkyl such as methyl, ethyl, n-propyl, isopropyl, n-butyl, i-butyl, sec-butyl, tert-butyl;

where the alkyl groups mentioned can be substituted by the following groups which, as a rule, do not increase the hydrophilicity, such as fluorine, hydroxyl, Cyano, —OCOR$^{12}$, —OR$^{10}$, —OCOOR$^{12}$, —CON(R$^{10}$)(R$^{11}$) or —OCONHR$^{12}$, in which R$^{12}$ is $C_1$–$C_{18}$alkyl such as methyl, ethyl, n-propyl, isopropyl, n-butyl, i-butyl, sec-butyl, tert-amyl, n-hexyl, 1,1,3,3-tetramethylbutyl, n-heptyl, n-octyl, n-nonyl, n-decyl, n-undecyl, n-dodecyl, n-octadecyl, 3-pentyl, 4-heptyl, 5-nonyl, 6-undecyl, 7-tridecyl, 3-hexyl, 3-heptyl, 3-nonyl, 3-undecyl, preferably $C_1$–$C_{12}$alkyl such as methyl, ethyl, n-propyl, isopropyl, n-butyl, sec-butyl, tert-butyl, tert-amyl, n-hexyl, n-heptyl, n-octyl, n-nonyl, n-decyl, n-undecyl, n-dodecyl, 3-pentyl, 4-heptyl, 5-nonyl, 6-undecyl, 7-tridecyl, 3-hexyl, 3-heptyl, 3-nonyl, 3-undecyl, $C_6$–$C_{10}$aryl such as phenyl and naphthyl, preferably naphthyl, or benzyl which is unsubstituted or substituted by halogen, such as chlorine and fluorine, preferably fluorine, $C_1$–$C_4$alkyl or —O-$C_1$–$C_4$-alkyl, or a five- to seven-membered heterocyclic radical such as pyridyl, pyrimidyl, pyrazinyl, triazinyl, furanyl, pyrrolyl, thiophenyl, quinolyl, isoquinolyl, coumarinyl, and R$^{10}$ and R$^{11}$ are hydrogen, $C_1$–$C_{18}$alkyl unsubstituted or substituted by the cyano or hydroxyl group as already mentioned above, preferably $C_1$–$C_{12}$alkyl, particularly preferably $C_1$–$C_8$alkyl, very particularly preferably $C_1$–$C_4$alkyl as already mentioned further above, $C_3$- to $C_{24}$cycloalkyl, preferably $C_5$-, $C_6$-, $C_{12}$-, $C_{15}$-, $C_{16}$-, $C_{20}$- and $C_{24}$cycloalkyl, aryl or heteroaryl, preferably derived from the abovementioned carbo- and heterocyclic aromatic radicals, in particular phenyl which is unsubstituted or substituted by halogen, $C_1$–$C_4$alkyl or $C_1$–$C_4$alkoxy, or in which R$^{10}$ and R$^{11}$ together with at least one of the other radicals R$^1$ to R$^8$ form a 5- to 6-membered ring or alternatively heterocyclic ring, for example a pyridine, pyrrole, furan or pyran ring.

In another preferred embodiment, substituents used on the alkyl groups are mono- or dialkylated amino groups, aryl radicals such as naphthyl or, in particular phenyl which is unsubstituted or substituted by halogen, alkyl or —O-alkyl, or furthermore heterocyclic aromatic radicals such as 2-thienyl, 2-benzoxazolyl, 2-benzothiazolyl, 2-benzimidazolyl, 6-benzimidazolonyl, 2-, 3- or 4-pyridinyl, 2-, 4- or 6-quinolyl or 1-, 3-, 4-, 6- or 8-isoquinolyl radicals.

If the substituents mentioned for their part in turn contain alkyl, this alkyl can be branched or unbranched and can preferably contain 1 to 18, in particular 1 to 12, especially 1 to 8 and particularly preferably 1 to 4, C atoms. Examples of unsubstituted alkyl groups are methyl, ethyl, n-propyl, isopropyl, n-butyl, sec-butyl, tert-butyl, tert-amyl, n-hexyl, 1,1,3,3-tetramethylbutyl, n-heptyl, n-octyl, n-nonyl, n-decyl, n-undecyl, n-dodecyl, n-octadecyl, 3-pentyl, 4-heptyl, 5-nonyl, 6-undecyl, 7-tridecyl, 3-hexyl, 3-heptyl, 3-nonyl, 3-undecyl, examples of substituted alkyl groups are hydroxymethyl, 2-hydroxyethyl, trifluoromethyl, trifluoroethyl, cyanomethyl, methoxycarbonylmethyl, acetoxymethyl or benzyl.

In the radical —OR$^9$, the following can be employed for R$^9$: hydrogen, $C_1$–$C_{18}$alkyl as already defined for R$^{12}$ including the preferred variants mentioned there. Examples of preferred radicals for R$^9$ which may be mentioned are: methyl, ethyl, n-propyl, isopropyl, n-butyl, sec-butyl, tert-butyl, tert-amyl, n-hexyl, 1,1,3,3-tetramethylbutyl, n-heptyl, n-octyl, n-nonyl, n-decyl, n-undecyl, n-dodecyl, n-octadecyl, 3-pentyl, 4-heptyl, 5-nonyl, 6-undecyl, 7-tridecyl, 3-hexyl, 3-heptyl, 3-nonyl, 3-undecyl, hydroxymethyl, 2-hydroxyethyl, trifluoromethyl, trifluoroethyl, cyanomethyl, methoxycarbonylmethyl, acetoxymethyl, benzyl, phenyl, o-, m- or p-chlorophenyl, o-, m- or p-methylphenyl, 1- or 2-naphthyl, cyclopentyl, cyclohexyl, cyclododecyl, cyclopentadecyl, cyclohexadecyl, cycloeicosanyl, cyclotetracosanyl, thienyl and pyranylmethyl. Examples of preferred radicals which may be mentioned are: hydroxyl, methoxy, —O-ethyl, —O-i-propyl-, —O-i-butyl, —O-phenyl, —O-2,5-di-tert-butylphenyl.

In —NR$^{10}$R$^{11}$ the radicals already defined above can be employed for R$^{10}$ and R$^{11}$. Examples of preferred radicals which may be mentioned are: amino, methylamino, dimethylamino, ethylamino, diethylamino, isopropylamino, 2-hydroxyethylamino, 2-hydroxypropylamino, N,N-bis(2-hydroxyethyl)amino, cyclopentylamino, cyclohexylamino, cyclododecylamino, cyclopentadecylamino, cyclohecadecylamino, cycloeicosanylamino, cyclotetracosanylamino, phenylamino, N-methylphenylamino, benzylamino, dibenzylamino, piperidyl or morpholyl, particularly preferred radicals are dimethylamino, diethylamino, di-n-propylamino, di-n-butylamino, di-n-pentylamino, di-n-hexylamino, di-n-heptylamino, di-n-octylamino, di-n-dodecylamino.

R$^{10}$ and R$^{11}$, on their own or, if appropriate, together with in each case at least one of the other free radicals from the set R$^1$, R$^2$, R$^3$, R$^4$, R$^5$, R$^6$, R$^7$, R$^8$ can form one or more five- or six-membered, saturated or unsaturated rings, such as pyridine, pyrrole, piperidine, quinoline or benzoquinolizine derivatives.

As —COR$^{12}$, those radicals can be employed in which R$^{12}$ is defined as indicated further above. Examples of preferred radicals R$^{12}$ which may be mentioned are: methyl, ethyl, n-propyl, isopropyl, n-butyl, sec-butyl, tert-butyl, tert-amyl, n-hexyl, 1,1,3,3-tetramethylbutyl, n-heptyl, n-octyl, n-nonyl, n-decyl, n-undecyl, n-dodecyl, n-octadecyl, 3-pentyl, 4-heptyl, 5-nonyl, 6-undecyl, 7-tridecyl, 3-hexyl, 3-heptyl, 3-nonyl, 3-undecyl, hydroxymethyl, 2-hydroxyethyl, trifluoromethyl, trifluoroethyl, cyanomethyl, methoxycarbonylmethyl, acetoxymethyl, benzyl, phenyl, o-, m- or p-chlorophenyl, o-, m- or p-methylphenyl, 1- or 2-naphthyl, cyclopentyl, cyclohexyl, cyclododecyl, cyclopentadecyl, cyclohexadecyl, cycloeicosanyl, cyclotetracosanyl, thienyl, pyranylmethyl and furfuryl.

As —NR$^{13}$COR$^{12}$, those radicals can be employed in which R$^{12}$ is defined as indicated further above, and R$^{13}$ is hydrogen, $C_1$–$C_{18}$alkyl, $C_3$–$C_{24}$cycloalkyl, $C_1$–$C_4$alkylaryl, each of which is unsubstituted or substituted by cyano-, hydroxyl or $C_1$–$C_4$alkoxycarbonyl groups, is $C_6$–$C_{10}$aryl which is unsubstituted or substituted by halogen, $C_1$–$C_4$alkyl or $C_1$–$C_4$alkoxy groups, or is a 5- to 7-membered heterocycle, where the meaning of the individual radicals such as alkyl, alkoxy aryl etc. corresponds to the definitions of these radicals indicated further above, including the preferred ranges indicated there, such as o-, m- or p-chlorophenyl, o-, m- or p-methylphenyl, 1- or 2-naphthyl, cyclopentyl, cyclohexyl, cyclododecyl, cyclopentadecyl, cyclohexadecyl, cycloeicosanyl, cyclotetracosanyl, thienyl, pyranylmethyl, benzyl or furfuryl. Examples of radicals which may be mentioned are: acetylamino, propionylamino, butyrylamino, benzoylamino, p-chlorobenzoylamino, p-methylbenzoylamino, N-methylacetamino, N-methylbenzoylamino, N-succinimido, N-phthalimido or N-(4-amino)phthalimido.

As $-NR^9COOR^{12}$, those radicals can be employed in which $R^{12}$ and $R^9$ are defined as already indicated further above. Examples of radicals which may be mentioned are: $-NHCOOCH_3$, $-NHCOOC_2H_5$ and $-NHCOOC_6H_5$.

As $-NR^9CONR^{10}R^{11}$, those radicals can be employed in which $R^{10}$, $R^{11}$ and $R^9$ are defined as already indicated further above. Examples of radicals which may be mentioned are: ureido, N-methylureido, N-phenylureido or N,N'-2',4'-dimethylphenylureido.

As $-NHSO_2R^{12}$, those radicals can be employed in which $R^{12}$ is defined as indicated further above. Examples of radicals which may be mentioned are: methylsulfonylamino, phenylsulfonylamino, p-tolylsulfonylamino or 2-naphthylsulfonylamino.

As $-SO_2R^{12}$, those radicals can be employed in which $R^{12}$ is defined as indicated further above. Examples of radicals which may be mentioned are: methylsulfonyl, ethylsulfonyl, phenylsulfonyl, 2-naphthylsulfonyl.

As $-SOR^{12}$, those radicals can be employed in which $R^{12}$ is defined as indicated further above. An example of a radical which may be mentioned is phenylsulfoxidyl.

As $-SO_2OR^{12}$, those radicals can be employed in which $R^{12}$ is defined as indicated further above. Examples of radicals $R^{12}$ which may be mentioned are: methyl, ethyl, phenyl, o-, m- or p-chlorophenyl, o-, m- or p-methylphenyl, 1-or 2-naphthyl.

As $-CONR^{10}R^{11}$, those radicals can be employed in which $R^{10}$ and $R^{11}$ are defined as already indicated further above. Examples of radicals which may be mentioned are: carbamoyl, N-methylcarbamoyl, N-ethylcarbamoyl, N-phenylcarbamoyl, N,N-dimethylcarbamoyl, N-methyl-N-phenylcarbamoyl, N-1-naphthylcarbamoyl or N-piperidylcarbamoyl.

As $-SO_2NR^{10}R^{11}$, those radicals can be employed in which $R^{10}$ and $R^{11}$ are defined as already indicated further above. Examples of radicals which may be mentioned are: sulfamoyl, N-methylsulfamoyl, N-ethylsulfamoyl, N-phenylsulfamoyl, N-methyl-N-phenylsulfamoyl or N-morpholylsulfamoyl.

As $-N=NR^{14}$, those radicals can be employed in which $R^{14}$ is the radical of a coupling component or a phenyl radical which is unsubstituted or substituted by halogen, alkyl or $-O$-alkyl, halogen and alkyl being defined as indicated above. Alkyl occurring in the definitions of $R^{14}$ can have one of the numbers of C atoms indicated further above as preferred. Examples of $R^{14}$ which may be mentioned are: the acetoacetarylide, pyrazolyl, pyridonyl, o-, p-hydroxyphenyl, o-hydroxynaphthyl, p-aminophenyl or p-N,N-dimethylaminophenyl radicals.

As $-OCOR^{12}$, those radicals can be employed in which $R^{12}$ is defined as indicated further above. Examples of radicals $R^{12}$ which may be mentioned are: methyl, ethyl, phenyl, o-, m- or p-chlorophenyl.

As $-OCONHR^{12}$, those radicals can be employed in which $R^{12}$ is defined as indicated further above. Examples of radicals $R^{12}$ which may be mentioned are: methyl, ethyl, phenyl, o-, m- or p-chlorophenyl.

Perylene-3,4:9,10-tetracarboxylic anhydrides II are known, for example, from the documents of the prior art mentioned at the outset. Substituted compounds are likewise known or can be prepared in analogy to, for example, the process described in DE-A 4,338,784. Thus nitro derivatives, for example, are obtainable by nitration with dinitrogen tetroxide in dichloromethane or copper nitrate in acetic anhydride. It is possible by the reduction of the nitro compounds to synthesize the corresponding amino compounds, which in turn can be further derivatized. Brominated derivatives can be prepared by direct bromination, for example analogously to DE-A 4,338,784; from these, as a rule, the corresponding alkoxy and phenoxy derivatives are accessible by nucleophilic substitution. Alkyl derivatives can be obtained in analogy to Leonhard Feiler, Dissertation 1995, University of Munich, by direct alkylation by means of alkyllithium compounds.

Particularly preferred derivatives are the unsubstituted perylene-3,4:9,10-tetracarboxylic anhydride II, in which the radicals $R^1$ to $R^8$ are hydrogen, and 1,7-disubstituted perylene-3,4:9,10-tetracarboxylic anhydrides II (e.g. described in DE-A 19547209, DE-A 19547210 or WO 96/22331).

Suitable sterically hindered amines are, for example, sterically hindered tertiary aliphatic amines having 7 to 20 carbon atoms, in particular non-condensing amines such as those which contain an isopropyl or a tert-butyl group, such as diethylisopropylamine, diisopropylmethylamine, tert-butyldiethylamine, di-tert-butylmethylamine, di-tert-butylethylamine or diisopropylethylamine, in particular diisopropylethylamine, secondary aliphatic amines having 4 to 20 carbon atoms such as 2-aminobutane, 2-amino-, 3-aminopentane, 2-amino-, 3-aminohexane, 2-amino-, 3-amino-, 4-aminoheptane, 3-amino-3-methylhexane, 3-amino-3-ethylpentane, 2-amino-, 3-amino-, 4-aminooctane, in particular 3-amino-3-ethylpentane, and also 1,4-diazabicyclo[2.2.2]octane ("DABCO"), diazabicycloundecene ("DBU") and heterocyclic amines such as tetramethylpiperidine, 2,6-lutidine or 2,6-di-tert-butylpyridine.

Customarily, the molar ratio of sterically hindered amine (=base) to perylene-3,4:9,10-tetracarboxylic anhydride II is chosen in the range from 0.5:1 to 20:1, preferably from 1:1 to 10:1, particularly preferably from 1.5:1 to 5:1.

The reaction is carried out according to the invention at elevated temperature, i.e. a temperature above room temperature. A preferred temperature range is one from 50 to 250° C., particularly preferably from 100 to 200° C., in particular from 160 to 190° C.

In a preferred embodiment, the reaction is carried out in the presence of an auxiliary base. Suitable auxiliary bases are, for example, cyclic basic nitrogen compounds consisting of a 5- or 6-membered ring, with, if desired, a fused phenyl ring having 4 to 9 carbon atoms, such as imidazole, 1-, 2- or 3-methylimidazole, pyridine or quinoline.

The molar ratio of auxiliary base to perylene-3,4:9,10-tetracarboxylic anhydride II is as a rule chosen in the range from 1:1 to 1:100, preferably from 1:10 to 1:50, particularly preferably from 1:25 to 1:50.

In a further, particularly preferred embodiment, the reaction is carried out in the presence of a catalyst such as a zinc, lead, calcium, copper, manganese, iron, cobalt, nickel, tin, silver or magnesium salt, preferably the chlorides, sulfates, nitrates and acetates, in particular zinc acetate, zinc propionate, lead acetate, calcium acetate, manganese acetate, cadmium acetate, iron(II) and iron(III) acetate, cobalt acetate, copper acetate, nickel acetate, tin acetate, silver acetate or magnesium acetate, particularly preferably zinc acetate dihydrate.

As a rule, a molar ratio of perylene-3,4:9,10-tetracarboxylic anhydride II to catalyst in the range from 1:0.5 to 1:10, in particular from 1:1 to 1:5, is used.

The reaction is customarily carried out at superatmospheric pressure, for example in a range from 120 kPa to 10 MPa, preferably in an autoclave, for example by heating the reaction mixture to the abovementioned temperature in an autoclave.

The reaction time naturally depends, inter alia, on the reaction temperature selected and the reactivity of the reactants and, at a reaction temperature of, for example, 170° C., is preferably in the range from 0.5 to 10 h, particularly preferably from 2 to 5 h.

In a particularly preferred embodiment, the perylene dianhydride II, particularly preferably the unsubstituted perylene dianhydride II ($R^1$ to $R^8$ are hydrogen), is reacted with diisopropylamine as a base in a molar ratio in the range from 1:3 to 1:5, preferably 1:3.5 to 1:4.5 (II/base) in the presence of zinc acetate dihydrate. In this procedure, as a rule no imide IV and, in only small amounts, the carboxylic acid III are obtained as by-products.

As a rule, the reaction mixture is worked up by taking up the amines present in an organic solvent, preferably a $C_1$–$C_4$alkanol such as methanol, ethanol, n-propanol, i-propanol or tert-butanol, particularly preferably ethanol, in the presence of an acid, preferably a dilute mineral acid such as dil. hydrochloric acid or dil. sulfuric acid, and separating them.

The insoluble residue is preferably treated with a base. A preferred embodiment consists in treating the residue with a concentrated alkali metal carbonate solution, preferably potassium carbonate, whereby the starting perylene II goes into solution as, for example, tetrapotassium salt, while because of the high addition of common ion the desired perylene anhydride I and also the perylene derivatives III and IV as a rule occurring as by-products remain undissolved. The insoluble constituents can be removed by known measures such as filtration or centrifugation of the soluble constituents. After acidifying, the tetrapotassium salt can be used again as a starting material.

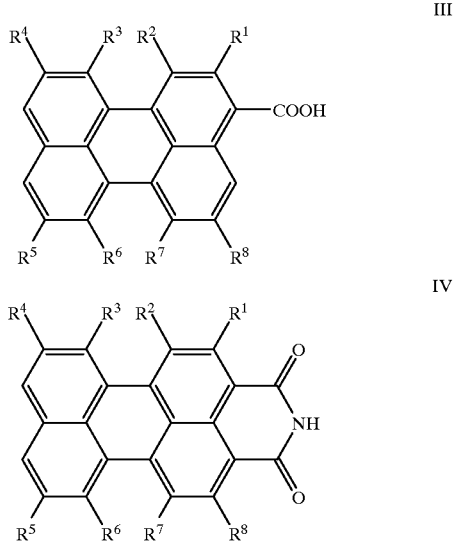

The desired perylene anhydride I can then be removed from the imide IV, for example by treating with dilute alkali metal carbonate solution, preferably with potassium carbonate, together with the perylene derivative III. The temperature of the potassium carbonate solution is preferably 40 to 95° C. If appropriate, this procedure must be repeated several times until the desired minimum amount of desired perylene anhydride I and/or carboxylic acid III in the residue is achieved.

Another preferred embodiment consists in treating the insoluble residue, free from amines, with dilute alkali metal carbonate solution, preferably with potassium carbonate solution, removing the soluble constituents from the insoluble matter in a manner known per se, and extracting the resulting aqueous basic phase with, for example, chloroform. The chloroform phase can be worked up or discarded, depending on economy and economical interests. The aqueous phase in general contains the desired perylene anhydride I and, if appropriate, depending on preparation conditions, the carboxylic acid III.

The solutions obtained according to the two embodiments, which contain the perylene anhydride III and, if appropriate, the carboxylic acid III, can be further worked up as follows: By acidifying, preferably with a dilute mineral acid such as dilute hydrochloric acid, the perylene anhydride I and, if appropriate, the carboxylic acid III are first precipitated and preferably extracted with n-butanol, particularly preferably with n-butanol which has a temperature in the range from 40 to 90° C. In the course of this, the carboxylic acid III usually goes into solution, and can thus be separated off and further purified, if appropriate by recrystallization, for example in chloroform. The desired perylene anhydride I remains as a residue which, if desired, can additionally be washed with water and subsequently dried.

A further embodiment of the present invention relates to the preparation of the carboxylic acid III by reaction of the perylene dianhydride II with a sterically hindered amine as a base at elevated temperature in the presence of water.

Sterically hindered amines which can be employed are the amines already mentioned further above, preferably the aliphatic amines, particularly preferably 3-amino-3-ethylpentane.

Customarily, the molar ratio of sterically hindered amine (=base) to perylene-3,4:9,10-tetracarboxylic anhydride II is chosen in the range from 0.5:1 to 20:1, preferably from 1:1 to 10:1, particularly preferably from 1.5:1 to 5:1.

Preferably, the molar ratio of perylene dianhydride II to water is chosen in the range from 20:1 to 0.5:1, particularly preferably from 10:1 to 2:1, very particularly preferably from 6:1 to 3:1.

The reaction is carried out according to the invention at elevated temperature, i.e. a temperature above room temperature. A preferred temperature range is one from 50 to 250° C., particularly preferably from 100 to 200° C., especially from 160 to 190° C.

In a preferred embodiment, the reaction is carried out in the presence of an auxiliary base. Suitable auxiliary bases are, for example, cyclic basic nitrogen compounds consisting of a 5- or 6-membered ring with, if appropriate, a fused phenyl ring having 4 to 9 carbon atoms, such as imidazole, 1,-2- or 3-methylimidazole, pyridine or quinoline.

As a rule, the molar ratio of auxiliary base to perylene-3,4:9,10-tetracarboxylic anhydride II is chosen in the range from 1:1 to 1:1 00, preferably from 1:10 to 1:50, particularly preferably from 1:25 to 1:50.

Working up is preferably carried out as already described further above, the carboxylic acid III preferably being recrystallized in chloroform/glacial acetic acid.

A particularly preferred embodiment relates to the reaction of the perylene dianhydride II with diisopropylamine as a base in the presence of water to give the carboxylic acid III.

A further embodiment relates to a process for the preparation of the perylene imide IV by reaction of the perylene dianhydride II with a sterically hindered amine as a base at elevated temperature.

Sterically hindered amines which can be employed are the amines already mentioned further above, preferably those which are not secondary or tertiary amines, but more labile amines compared therewith can be mentioned such as DABCO and DBU.

In a preferred embodiment, the molar ratio of sterically hindered amine (=base) to perylene-3,4:9,10-tetracarboxylic anhydride II is chosen in the range from 0.5:1 to 20:1, preferably from 1:1 to 10:1, particularly preferably from 1.5:1 to 5:1.

The reaction is carried out according to the invention at elevated temperature, i.e. a temperature above room temperature. A preferred temperature range is one from 50 to 250° C., particularly preferably from 100 to 200, in particular from 160 to 190° C.

In a preferred embodiment, the reaction is carried out in the presence of an auxiliary base. Suitable auxiliary bases are, for example, cyclic basic nitrogen compounds consisting of a 5- or 6-membered ring with, if appropriate, a fused phenyl ring having 4 to 9 carbon atoms, such as imidazole, 1-, 2- or 3-methylimidazole, pyridine or quinoline.

As a rule, the molar ratio of auxiliary base to perylene-3,4:9,10-tetracarboxylic anhydride II is chosen in the range from 1:1 to 1:100, preferably from 1:10 to 1:50, particularly preferably from 1:25 to 1:50.

Working up is preferably carried out as already described further above, the perylene imide IV—as already described—being obtained from the alkali metal carbonate extractions as an insoluble residue. The product can be further purified from this residue by recrystallization, if desired in chloroform/ethanol.

In a particularly preferred embodiment, the perylenedianhydride II is reacted with DABCO in the molar ratio 1:2 to 1:4 observing the reaction conditions already mentioned further above. In this case, according to previous observations, the carboxylic acid III occurring as a by-product is only formed in small amounts, if at all.

A further embodiment of the present invention relates to substituted perylene anhydrides I, i.e. perylene anhydrides I in which at least one of the radicals $R^1$ to $R^8$ is other than hydrogen, in particular those substituted perylene anhydrides I which are substituted in the 1-, 1,6-, 1,7-, 2,5-, 7,12- or 8,11-positions, i.e. in which the radicals $R^2$; $R^2,R^7$; $R^2,R^6$; $R^1,R^8$; $R^3,R^6$ and $R^4,R^5$ in each case are not hydrogen. The substituted perylene anhydrides I preferably have one or two substituents in the ring system, and in the case of disubstituted compounds the substituents are preferably identical.

Suitable substituents are the radicals $R^1$ to $R^8$ already mentioned further above, preferred substituents are the alkyl, nitro, amino radicals mentioned there and halogen such as chlorine or bromine.

A further embodiment of the present invention relates to substituted perylenecarboxylic acids III, in particular those substituted carboxylic acids III which are substituted in the 1-, 1,6- ,1,7-, 2,5-, 7,12- or 8,11-positions. The substituted perylenecarboxylic acids III have one or two substituents in the ring system, and in the case of disubstituted compounds the substituents are preferably identical.

Suitable substituents are the radicals $R^1$ to $R^8$ already mentioned further above, preferred substituents are the alkyl, nitro, amino radicals mentioned there and halogen such as chlorine or bromine.

A further embodiment of the present invention relates to substituted perylene imides IV, in particular those substituted perylene imides IV which are substituted in the 1-, 1,6-, 1,7-, 2,5-, 7,12- or 8,11-positions. The substituted perylene anhydrides I preferably have one or two substituents in the ring system, and in the case of disubstituted compounds the substituents are preferably identical.

Suitable substituents are the radicals $R^1$ to $R^8$ already mentioned further above, preferred substituents are the alkyl, nitro, amino radicals mentioned there and halogen such as chlorine or bromine.

The perylene derivatives I and II according to the invention and their metal complexes are suitable for use as colouring agents, in particular as pigments and dyes, as a rule by methods known per se in each case, preferably (a) for the mass-dyeing of polymers, where as polymers polyvinyl chloride, cellulose acetate, polycarbonates, polyamides, polyurethanes, polyimides, polybenzimidazoles, melamine resins, silicones, polyesters, polyethers, polystyrene, poly(methyl methacrylate), polyethylene, polypropylene, poly(vinyl acetate), polyacrylonitrile, polybutadiene, polychlorobutadiene or polyisoprene or the copolymers of the monomers mentioned can be employed;

(b) as vat dyes or mordant dyes, e.g. for the dyeing of natural substances as well as, in particular, of paper, wood, straw, leather, hides or natural fibre materials such as cotton, wool, silk, jute, sisal, hemp, flax or animal hair (e.g. horsehair) and their transformation products such as the viscose fibres, nitrate silk or cuprammonium rayon (rayon), preferred salts for the mordant being aluminium, chromium and iron salts;

(c) in the production of dyes, coatings, in particular automotive coatings, paints, paper colours, printing colours, inks, in particular for use in ink-jet printers, preferably in homogeneous solution as fluorescent ink, and for marking and writing purposes, as well as in electrophotography, e.g. for dry copier systems (Xerox process) and laser printers;

(d) for security marking purposes such as for cheques, cheque cards, banknotes, coupons, documents, identification papers and the like in which a specific, unmistakable colour imprint is to be achieved;

(e) as an additive to colouring agents such as pigments and dyes, in which a specific colour hue is to be achieved, particularly luminescent colour shades are preferred;

(f) for the marking of objects for the mechanical recognition of these objects by means of fluorescence, the mechanical recognition of objects for sorting is preferred, e.g. also for the recycling of plastics, where alphanumeric imprints or bar codes are preferably employed;

(g) for the frequency conversion of light, e.g. in order to make longer-wave, visible light from short-wave light or for the frequency doubling and frequency tripling of laser light in non-linear optics;

(h) for the production of display elements for a variety of display, indication and marking purposes, e.g. passive display elements, indication and traffic signs, such as traffic lights;

(i) as a starting material for superconducting organic materials (via π-π interactions, after doping with, for example, iodine an intermediate charge delocalization is customarily obtained);

(j) for solid fluorescence labelling;

(k) for decorative and artistic purposes;

(I) for tracer purposes, e.g. in biochemistry, medicine, technology and natural science, it being possible to couple the dyes according to the invention covalently with substrates or via secondary valences such as hydrogen bridge bonds or hydrophobic interactions (adsorption);

(m) as fluorescent dyes in highly sensitive detection procedures (see C. Aubert, J. Fünfschilling, 1. Zschokke-Granacher and H. Langhals, Z. Analyt. Chem. 1985, 320, 361), in particular as fluorescent dyes in scintillators;

(n) as dyes or fluorescent dyes in optical light collection systems, in fluorescent solar collectors (see H. Langhals, Nachr. Chem. Tech. Lab. 1980, 28, 716), in fluorescence-activated displays (see W. Greubel and G. Baur, Elektronik 1977, 26, 6), in cold light sources for light-induced polymerization for the preparation of plastics, for materials testing, e.g. in the production of semiconductor circuits, for the investigation of microstructures of integrated semiconductor components, in photoconductors, in photographic procedures, in display, illumination or image converter systems in which the excitation takes place by means of electrons, ions or UV radiation, e.g. in fluorescent displays, cathode ray tubes or in fluorescent tubes, as part of an integrated semiconductor circuit which contains dyes as such or in combination with other semiconductors, e.g. in the form of an epitaxy, in chemiluminescence systems, e.g. in chemiluminescence flashlights, in luminescence immunassays or other luminescence detection procedures, as signal dyes, preferably for the optical accentuation of handwriting and drawings or other graphical products, for the marking of labels and other articles on which a particular optical colour imprint is to be achieved, in dye lasers, preferably as fluorescent dye lasers, for the production of laser beams, as an optical storage medium and as Q switches;

(o) and also as rheology enhancers.

EXAMPLES

Example 1

Perylene-3,4-dicarboxylic anhydride I

Perylene-3,4:9,10-tetracarboxylic bisanhydride II (2.00 g, 5.1 mmol), diisopropylethylamine (2.63 g, 20.4 mmol), zinc acetate dihydrate (1.49 g, 6.8 mmol) and imidazole (16 g, 235 mmol) are finely ground and heated to 170° C. for 3.5 h in a stainless steel autoclave. The reaction mixture is dispersed in hot ethanol (240 ml), 2N HCl is added (450 ml) and the precipitate is filtered off with suction and dried in air at 110° C. It is treated in six cycles with hot 2N $K_2CO_3$ solution (250 ml) which is then extracted with chloroform. The chloroform phase is discarded and the aqueous phase is acidified with 2N HCl. The precipitate is filtered off with suction and dried in air at 110° C. It is treated with 1-butanol at 100° C., washed with dist. water and dried in air again at 100° C. Yield 410 mg (25%) of pure 1, m.p.>350° C.—$R_f$ (silica gel; chloroform/glacial acetic acid 10:1)=0.78.

Examples 2 to 4

Example 1 is repeated with the difference that no zinc acetate is added and both the amine and the molar ratio of perylene dianhydride II to amine are varied according to the table below.

Example 5

Perylene-3-carboxylic acid III

Perylene-3,4:9,10-tetracarboxylic bisanhydride II (2.00 g, 5.1 mmol), diisopropylethylamine (2.63 g, 20.4 mmol), distilled water (20 ml) and imidazole (16 g, 235 mmol) are reacted and worked up as described in Example 1 for the preparation of I. The 1-butanol phase is evaporated and the residue is recrystallized from chloroform/glacial acetic acid (10:1). Yield 360 mg (24%) of III, m.p. 320° C.—$R_f$ (silica gel; chloroform/ethanol 10:1)=0.41. —IR (KBr): v=3410 $cm^{-1}$ m, 3051 w, 1680 s, 1590 m, 1569 m, 1502 m, 1492 m, 1258 m, 1215 w, 1189 m, 1151 m, 812 s, 767 s.—UV/Vis ($CHCl_3$): $\lambda_{max}$ ($E_{rel}$)=453.3 nm (1.00), 439.5 (0.92).—Fluorescence ($CHCl_3$): $\lambda_{max}$=492 nm.—$^1$H NMR ([$D_6$]-DMSO): δ=8.81 (s, 1H, $CO_2H$), 8.29 (m, 7H), 7.77 (m, 2H), 7.43 (m, 2H). —MS (70 eV): m/z (%)=296 (100) [$M^+$], 252 (8.2) [$M^+-CO_2$], 250 (23.4), 125 (16.1).

Example 6

Perylene-3,4-dicarboximide IV

Perylene-3,4:9,10-tetracarboxylic bisanhydride II (2.00 g, 5.1 mmol), DABCO (1.14 g, 10.2 mmol) and imidazole (16 g, 235 mmol) are reacted and worked up as described in Example 1 for the preparation of I. The insoluble residue from the $K_2CO_3$ extractions is dried in air at 110° C. and then recrystallized extractively from chloroform/ethanol 10:1. Yield 1.24 g (76%) of IV, m.p.>350° C.—$R_f$ (silica gel; chloroform/glacial acetic acid 10:1): 0.55. —IR (KBr): v=3423 $cm^{-1}$ m, 3050 w, 1628 s, 1590 s,1569 s, 1364 s, 1290 m, 1273 m, 1137 w, 1060 w, 812 m, 764 m. —UV/Vis ($CHCl_3$): $\lambda_{max}$ ($\epsilon_{rel}$)=488.2 (1.00), 509.0 (0.96).—UV/Vis (DMSO): $\lambda_{max}$ ($\epsilon$)=466.5 (10600), 492.3 (12030). —Fluorescence ($CHCl_3$): $\lambda_{max}$=544 nm, 572. —MS (70 eV): m/z (%)=321 (100) [$M^+$], 277 (10) [$M^+-CO_2$], 250 (9) [$M^+-CO_2-HCN$], 146(8),125 (10).

Examples 7 and 8

Example 6 is repeated with the difference that in Example 8 DBU is employed instead of DABCO and the molar ratios of perylene dianhydride II to employed amine are varied according to the table below.

TABLE

Summary ot the results of Examples 1 to 8

| Ex. | Amine | Yields of % I | % III | % IV | Molar ratio II/amine | Additives |
|---|---|---|---|---|---|---|
| 1 | Diisopropylethylamine | 25 | 4 | 0 | 1:4 | Zn(OAc)$_2$ |
| 2 | 3-Amino-3-ethylpentane | 11 | 5 | 61 | 1:2 | — |
| 3 | Diisopropylethylamine | 8 | 0 | 0 | 1:1 | — |
| 4 | Diisopropylethylamine | 12 | 5 | 0 | 1:2 | — |
| 5 | Diisopropylethylamine | 5 | 24 | 0 | 1:4 | H$_2$O |
| 6 | DABCO | 16 | 2 | 76 | 1:2 | — |
| 7 | DABCO | 24 | 0 | 76 | 1:4 | — |
| 8 | DBU | 16 | 5 | 50 | 1:1 | — |

What is claimed is:

1. A process for the preparation of perylene-3,4-dicarboxylic anhydrides of the formula I

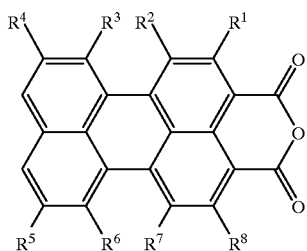

in which $R^1$, $R^2$, $R^3$, $R^4$, $R^5$, $R^6$, $R^7$, $R^8$ are hydrogen, or one radical to eight radicals are a radical selected from the group consisting of an unsubstituted or substituted carbocyclic aromatic radical, an unsubstituted or substituted heterocyclic aromatic radical, halogen, unsubstituted or substituted $C_1$–$C_{18}$alkyl, —$OR^9$, —CN, —$NR^{10}R^{11}$, —$COR^{12}$, —$NR^{13}COR^{12}$, —$NR^9COOR^{12}$, —$NR^9CONR^{10}R^{11}$, —$NHSO_2R^{12}$, —$SO_2R^{12}$, —$SOR^{12}$, —$SO_2OR^{12}$, $CONR^{10}R^{11}$, —$SO_2NR^{10}R^{11}$, —N=$NR^{14}$, —$OCOR^{12}$ and —$OCONHR^{12}$, where each two adjacent radicals together can form a carbocyclic or heterocyclic ring, where $R^{12}$ is $C_1$–$C_{18}$alkyl, $C_6$–$C_{10}$aryl or benzyl which is unsubstituted or substituted by halogen, $C_1$–$C_4$alkyl or $C_1$–$C_4$alkoxy or is a five- to seven-membered heterocyclic radical, $R^{10}$ and $R^{11}$ independently of one another are hydrogen, $C_1$–$C_{18}$alkyl, $C_3$–$C_{24}$cycloalkyl, $C_6$–$C_{10}$-aryl or 5- to 7-membered heteroaryl, each of which is unsubstituted or substituted by cyano or hydroxyl groups, or in which $R^{10}$ and $R^{11}$ together with at least one of the other radicals $R^1$ to $R^8$ form a 5- or 6-membered carbocyclic or heterocyclic ring, $R^9$ is hydrogen, $C_1$–$C_{18}$alkyl, $C_3$–$C_{24}$cycloalkyl, $C_6$–$C_{10}$aryl or 5- to 7-membered heteroaryl, $R^{13}$ is hydrogen, $C_1$–$C_{18}$alkyl, $C_3$–$C_{24}$cycloalkyl, $C_1$–$C_4$alkylaryl, each of which is unsubstituted or substituted by cyano, hydroxyl or $C_1$–$C_4$alkoxycarbonyl groups, is $C_6$–$C_{10}$aryl which is unsubstituted or substituted by halogen, $C_1$–$C_4$alkyl or $C_1$–$C_4$alkoxy groups, or is a 5- to 7-membered heterocycle, and $R^{14}$ is the radical of a coupling component or $C_6$–$C_{10}$aryl which is unsubstituted or substituted by halogen, $C_1$–$C_4$alkyl or $C_1$–$C_4$alkoxy groups, which comprises reacting perylene-3,4:9,10-tetracarboxylic anhydride of the formula II

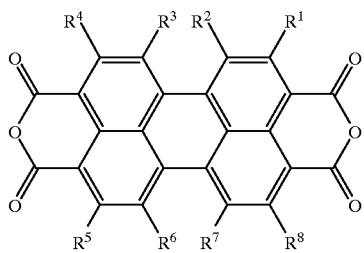

in which $R^1$ to $R^8$ have the meaning indicated above, with a sterically hindered amine as a base at elevated temperature.

2. A process according to claim 1, wherein the unsubstituted perylene-3,4:9,10-tetracarboxylic anhydride of the formula 11 is employed.

3. A process according to claim 1, wherein the reaction is carried out in the presence of a catalyst.

4. A process according to claim 2, wherein the reaction is carried out in the presence of a catalyst.

5. A process according to claim 1, wherein the reaction is carried out in the presence of an auxiliary base.

6. A process according to claim 2, wherein the reaction is carried out in the presence of an auxiliary base.

7. A process according to claim 3, wherein the reaction is carried out in the presence of an auxiliary base.

8. A process for the preparation of the perylenecarboxylic acid of the formula III

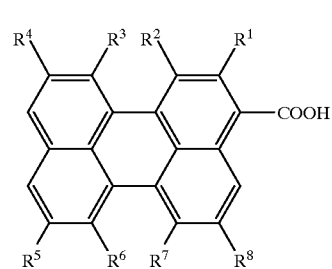

in which the radicals $R^1$ to $R^8$ have the same meaning as defined in claim 1, which comprises reacting a perylene dianhydride II according to claim 1 with a sterically hindered amine as a base at elevated temperature in the presence of water and, if desired, of an auxiliary base.

9. A process for the preparation of the perylene imide of the formula IV

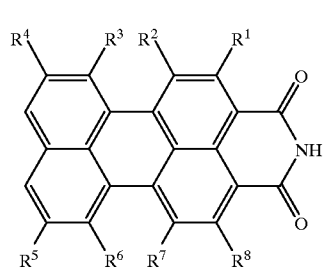

in which the radicals $R^1$ to $R^8$ have the same meaning as defined in claim 1, which comprises reacting a perylene dianhydride II according to claim 1 with a sterically hindered amine as a base at elevated temperature and, if desired, in the presence of an auxiliary base.

10. A perylene anhydride of the formula I as defined under claim 1, at least one of the radicals $R^1$ to $R^8$ being other than hydrogen, preferably those substituted perylene anhydrides I which are substituted in the 1-, 1,6- ,1,7-, 2,5-, 7,12- or 8,11-positions.

11. A perylenecarboxylic acid of the formula III as defined under claim 8, at least one of the radicals $R^1$ to $R^8$ being other than hydrogen, preferably those in which the 1-, 1,6-, 1,7-, 2,5-, 7,12- or 8,11-positions are substituted.

* * * * *